United States Patent [19]

Jones et al.

[11] Patent Number: 5,918,597
[45] Date of Patent: Jul. 6, 1999

[54] PEEP CONTROL IN A PISTON VENTILATOR

[75] Inventors: Michael B. Jones, Excelsior; Eric Bailey, Roseville; David B. Lura, Brooklyn Park, all of Minn.

[73] Assignee: Nellcor Puritan Bennett, Pleasanton, Calif.

[21] Appl. No.: 09/007,426

[22] Filed: Jan. 15, 1998

[51] Int. Cl.$^6$ ................................................. A61M 16/00
[52] U.S. Cl. .............................. 128/205.18; 128/204.23; 128/204.26
[58] Field of Search ........................ 128/205.18, 204.21, 128/204.18, 205.14, 205.15, 205.16, 205.17, 200.14, 204.23, 204.26

[56] References Cited

U.S. PATENT DOCUMENTS

| | | |
|---|---|---|
| 3,741,208 | 6/1973 | Jonsson et al. . |
| 4,022,234 | 5/1977 | Dobritz . |
| 4,023,587 | 5/1977 | Dobritz . |
| 4,323,064 | 4/1982 | Hoenig et al. . |
| 4,527,557 | 7/1985 | DeVries et al. . |
| 4,561,287 | 12/1985 | Rowland . |
| 4,794,922 | 1/1989 | DeVries . |
| 5,072,729 | 12/1991 | DeVries . |
| 5,150,291 | 9/1992 | Cummings et al. . |
| 5,161,525 | 11/1992 | Kimm et al. . |
| 5,237,987 | 8/1993 | Anderson et al. . |
| 5,271,389 | 12/1993 | Isaza et al. . |
| 5,299,568 | 4/1994 | Forare et al. . |
| 5,319,540 | 6/1994 | Isaza et al. . |
| 5,323,772 | 6/1994 | Linden et al. ................ 128/204.23 |
| 5,331,995 | 7/1994 | Westfall et al. . |
| 5,383,449 | 1/1995 | Forare et al. . |
| 5,390,666 | 2/1995 | Kimm et al. . |
| 5,494,028 | 2/1996 | DeVries et al. . |
| 5,524,615 | 6/1996 | Power . |
| 5,531,221 | 7/1996 | Power et al. ................ 128/205.18 |
| 5,666,945 | 9/1997 | Davenport ................... 128/200.14 |
| 5,797,393 | 8/1998 | Kohl ............................ 128/204.23 |

FOREIGN PATENT DOCUMENTS

WO 9624402   8/1996   WIPO .

OTHER PUBLICATIONS

Dräger Inc. Critical Care Systems—Minimum Pressure Ventilation brochure.
Newport Medical Instruments, Inc.—Newport Wave VM200 brochure; Feb. 1995.
Newport Medical Instruments, Inc.—The Newport Breeze EI50 Ventilator brochure; Mar. 1996.
Allied Healthcare Products, Inc.—The Bear 1000 Ventilator with Smart Trigger brochure; 1996.
Healthdyne Technologies—Quantum PSV brochure.
Bird Products Corporation—TBird AVS Advanced Ventilatory System brochure; Jan. 1996.
Healthdyne International—Quantum PSV brochure.
Respironics Inc.—BiPAP Vision System brochure; 1996.
Lifecare International, Inc.—PLV–102 brochure; Jan. 1995.
Air Liquide Healthcare—Taema Monnal DCC brochure.
Bird Products Corporation—TBird VS TBird VSO$_2$ Ventilatory System brochure; Jan. 1996.

*Primary Examiner*—John G. Weiss
*Assistant Examiner*—Charles W. Anderson
*Attorney, Agent, or Firm*—Hovey, Williams, Timmons & Collins

[57] ABSTRACT

A piston ventilator is provided which advantageously monitors the positive end expiratory pressure (PEEP) in a patient circuit for supplying breathable gas to a patient, and controls a shiftable valve element in an exhalation valve to regulate the amount of resistance during the exhalation portion of the patient's breath. The shiftable element is preferably an inflatable diaphragm which receives a pneumatic signal through a signal conduit. The pressure provided by the signal conduit is controlled by the amount of gas vented by a PEEP valve, wherein the greater the opening of the PEEP valve, the greater the amount of gas from the patient circuit is vented therethrough and consequently the less the restriction is provided in the exhalation valve. The primary source of pressure for the breathable gas is provided by a piston ventilator, with make-up pressurization in the patient circuit provided by a secondary source such as a blower to compensate for leakage and to provide pressurization for the signal conduit during the retraction of the piston within the cylinder and consequent exhalation portion of the patient's breath. Supplemental oxygen is provided to the patient circuit during retraction of the piston to ensure adequate oxygen enrichment at the incipient portion of the inhalation portion of the patient's breath.

16 Claims, 2 Drawing Sheets

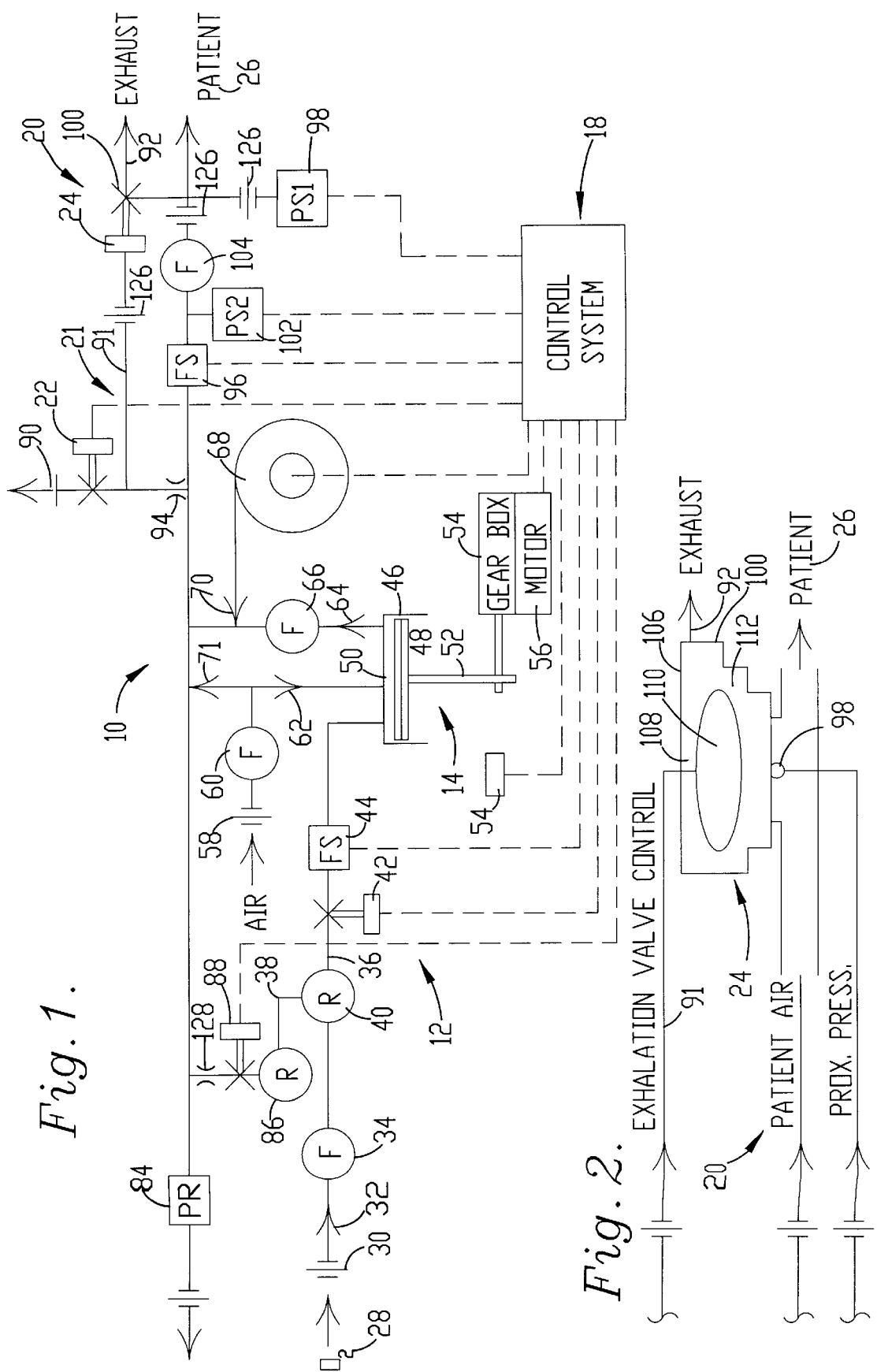

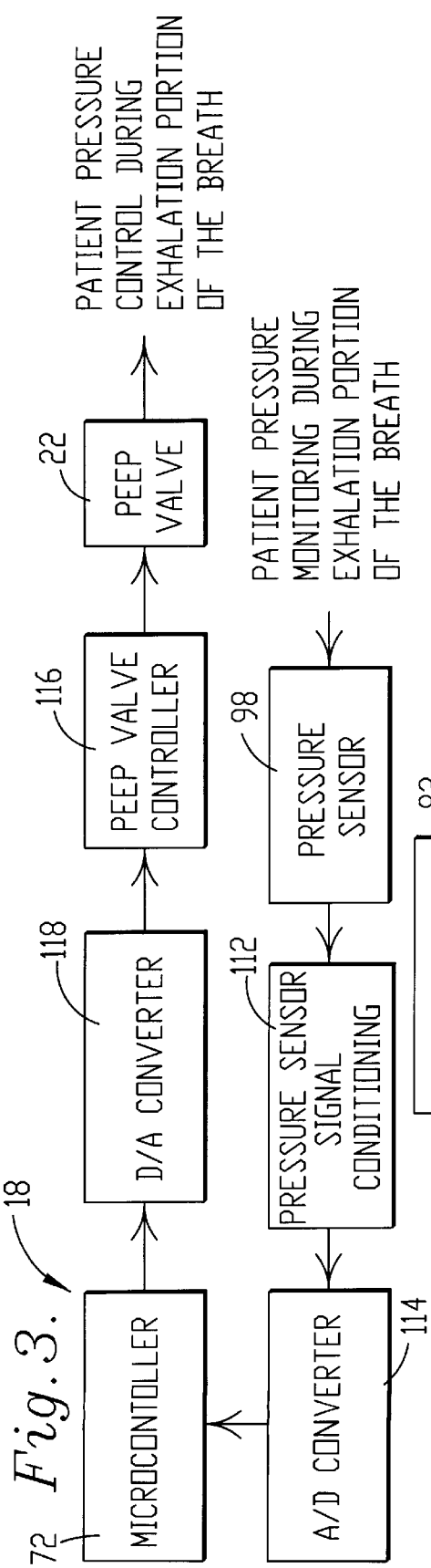
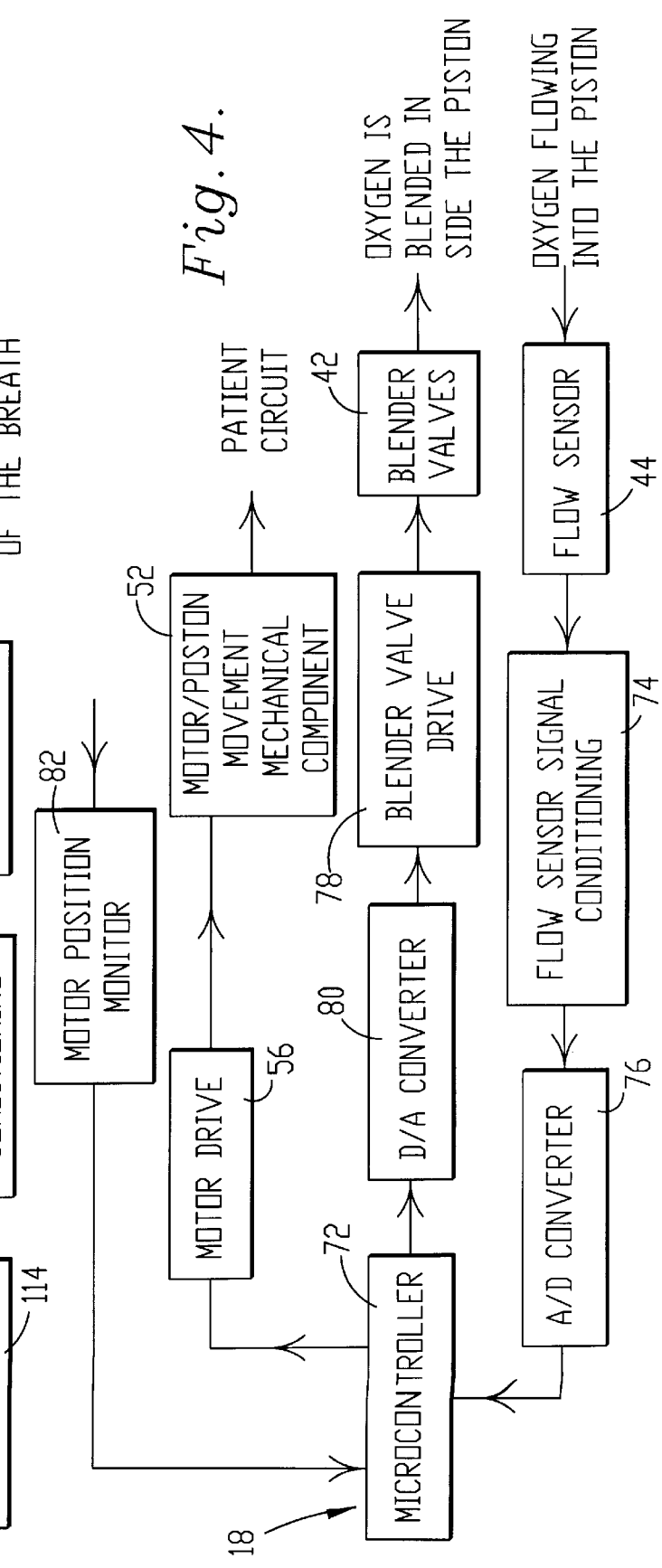

PEEP CONTROL IN A PISTON VENTILATOR

BACKGROUND OF THE INVENTION

1. Field of the Invention

This invention relates to positive end expiratory pressure (PEEP) control in a piston ventilator for controlling the residual pressure in the patient's lungs during retraction through an exhalation valve through closed loop pressure support in an exhalation control system by adjusting a signal corresponding to pneumatic pressure delivered to an exhalation valve in the patient circuit. The closed loop PEEP control maintains a pressure in the patient circuit during the expiratory phase of the breath by adjusting the pneumatic pressure on the exhalation valve as it relates to the pneumatic pressure in the patient circuit. More particularly, it is concerned with a system using a PEEP control valve which selectively vents gas to control the pressure in a signal line coupled with the exhalation valve, the opening of the PEEP control valve being dependent on a PEEP signal detected by a sensor in the exhalation control system in communication with the patient circuit.

2. Description of the Prior Art

Ventilators of the type concerned herein are designed to supply air or other breathable gases to assist a patient in breathing, and particularly to provide pressurized air to aid patients requiring respiratory assistance. In some circumstances, mandatory breath patterns are supported by the ventilator, while in others, a spontaneous breath pattern is supported. In addition, it is often desirable to provide supplemental oxygen to enrich the oxygen content of the gas inhaled by the patient.

An oxygen concentrator having a reservoir for receiving oxygen-enriched gas, including a sensor for monitoring withdrawal of the enriched gas from the reservoir, and a microprocessor for determining the minimum time for charging of the gas to provide a product gas with a selected oxygen concentration at the sensed rate of withdrawal is shown in U.S. Pat. No. 4,561,287. Another system for mixing the oxygen with air or another gas in a ventilation system in predetermined proportions involves the use of separate inlets into a pressure vessel up to respective first and second pressures is described in U.S. Pat. Nos. 4,022,234 and 4,023,587. The system shown therein operates in alternating withdrawal and mixing cycles. A feedback control of the rate of flow and pressure of breathing gas to a patient by an inspiration servounit is described in U.S. Pat. No. 3,741,208. U.S. Pat. No. 5,383,449 provides for control of oxygen concentration in a breathable gas by calculation of the mole ratios and pressure in the containment vessel, and by sequentially injecting oxygen and another gas to desired pressure values. These so-called batch mixing ventilators represent one system for patient ventilation.

While such systems are very useful in hospitals and other health care facilities, smaller and more confined devices not requiring connection to pressurized air are often more appropriate for home care. Piston and bellows types of ventilators allow delivery of a predetermined volume of breathing gas at a desired pressure responsive to the initiation of inspiratory efforts by a patient. Piston based ventilators can typically be made to be more compact than bellows based ventilators, but piston ventilators typically blend pressurized air and oxygen in a high pressure blender. The resultant mixture is then drawn by a piston through a valve that reduces the pressure of the mixture. Such systems typically do not permit the use of room air and pressurized oxygen, and can result in some risk of overpressurization in the event of failure of a high pressure gas delivery valve controlling introduction of one of the breathing gas components into the high pressure blender.

Another system for blending oxygen in a ventilator is shown in International Publication No. WO 96/24402 published Aug. 15, 1996. This system is designed for mixing gases at approximately ambient atmospheric pressure, such as oxygen and air. The mixing apparatus includes a piston disposed within a pump chamber. A flow limiting inlet controls introduction of oxygen for mixing with air, and the pressure of the oxygen is limited to an acceptable maximum pressure whereby even if the oxygen valve fails, the breathing gas will not be provided at an excessive pressure. A demand valve is alternately provided for reducing the pressure of the oxygen supplied before mixing, and a pressure sensor is also provided downstream of the demand valve for detecting failure of the demand valve to shut off the supply of the oxygen to prevent overpressurization.

The positive end expiratory pressure (PEEP) is the pressure in the breathing circuit in close proximity to the patient during the exhalation phase of the breath. It is known to select a PEEP for ventilators operating in a spontaneous breath pattern, as set forth in U.S. Pat. No. 5,383,449. However, the use of the PEEP value in ventilators, particularly piston-type ventilators, has been limited to controlling the mode of operation, e.g. the exhalation valve being fully open for mandatory breath patterns or fully closed for spontaneous breath patterns.

It would therefore be desirable to provide an exhalation control system, particularly in a piston-type ventilator, which would permit regulation of the amount of restriction provided by the exhalation valve to promote or prompt the patient to take the next breath following at the end of exhalation and the commencement of inhalation.

SUMMARY OF THE INVENTION

These and other objects are largely met by the use of PEEP control in a piston ventilator in accordance with the present invention. That is to say, the exhalation control system of the present invention advantageously monitors the PEEP and regulates the exhalation control valve to increase or decrease the resistance to the exhalation phase of the breath of the patient, thereby permitting the patient to expend some, but not all, of the effort necessary to exhale. The present invention uniquely accomplishes this result through the use of an exhalation control valve which is provided with a diaphragm which can partially restrict the exhaust opening through pneumatic regulation. The PEEP control exhalation system is incorporated as a part of a ventilator as described herein.

The piston ventilator of the present invention broadly includes an oxygen blending module, a primary piston-driven pressurization system, a secondary make-up gas module, a controller, an exhalation control system and a patient circuit for delivering air to the patient for inhalation. The oxygen blending module includes a connection to a source of pressurized oxygen, a first control valve which regulates the flow of oxygen to the piston, and a flow sensor for monitoring the flow of oxygen to the piston. In addition, the oxygen blending module includes a second control valve for regulating the amount of oxygen delivered to the patient circuit to enrich the gas remaining in the patient circuit during the retraction stroke of the piston. The valves are preferably current-controlled sensitive orifice valves responsive to signals from the controller, which preferably includes a microprocessor. The flow sensor is operatively connected to the controller to provide signals corresponding to the flow of oxygen to the primary piston-driven pressurization system.

The primary piston-driven pressurization system receives oxygen from the oxygen blending module and air or another breathable gas and is operated by a motor, gear drive and cam arm to provide a sinusoidal flow during intake and, under certain operating parameters, a sinusoidal flow of blended gas therefrom. That is to say, when relatively large volumes of gas are delivered by the piston and cylinder assembly, the piston-driven system delivers a low volumetric flow of blended gas at the beginning of its protracting stroke building to a maximum volumetric flow of blended gas during the intermediate portion of its protracting stroke and then reducing to a low volumetric flow of gas at the end of its protracting stroke before beginning the retracting stroke, which is similarly sinusoidal. When the volume of gas to be provided to the patient circuit is relatively low, the flow will increase abruptly and then reduce to a small flow at the end of the protracting stroke.

Because the increase of the volume above the piston in the cylinder is non-linear but rather sinusoidal, during intake and blending the flow of the oxygen into the cylinder is similarly non-linear. The motor driving the piston preferably provides a virtually continuously updated signal to the controller corresponding to the position of the piston, which permits the microprocessor to calculate by integration the volume of gas in the cylinder during the retraction stroke and similarly the volume of added oxygen which should have passed by the flow sensor and present in the cylinder. By continuously updating the comparison between the calculated amount of oxygen in the cylinder with the actual amount of oxygen delivered to the cylinder during the retraction stroke, the controller can substantially continuously signal the first control valve to open or close to provide the desired amount of oxygen enrichment to the cylinder. Preferably, the motor is a motor capable of bi-directional movement with the corresponding stroke of the piston being adjustable using an adjustable end-of-travel sensor to initialize the stroke of the piston by signaling the controller to provide a signal to the motor to reverse direction between protraction and retraction and thereby accommodate users of different lung capacities.

The secondary make-up module uses a low-pressure blower to provide make-up air or other breathable gas to the system to compensate for leakage, in particular the leakage from around tracheal tubes inserted into the patient's windpipe or mouth. The controller provides a speed control signal to the blower to maintain the appropriate amount of pressure in the patient circuit based upon the amount of flow out of the patient circuit. The controller senses the amount of flow out of the patient circuit, which in turn operates an oxygen valve to maintain a satisfactory oxygen enriched gas in the patient circuit. The primary flow sensor provides a signal corresponding to the volume of mixed gas leakage in the patient circuit ($V_T$). The volume of oxygen ($O_2$) introduced is known by introducing $O_2$ gas of known pressure upstream of a known orifice size for a specific period of time, yielding an oxygen volume ($V_{O2}$).

The concentration of oxygen in the make-up gas is then known by the equation:

$$V_T = V_{AIR} + V_{O2}$$
$$O_2\% = 79 \ (V_{O2} \div V_T) + 21$$

where $V_T$ is known by the measurement obtained by the primary flow restrictor and $V_{O2}$ is known by how long the primary oxygen valve is open, the orifice size, and the upstream pressure.

The exhalation control system is positioned upstream from the patient circuit for the ventilator and includes a flow sensor for monitoring the flow of breathable gas to the patient, pressure sensors for detecting the pressure in the patient circuit during inhalation and exhalation, a positive end expiratory pressure control valve, and a flow restrictor. The positive end expiratory pressure (PEEP) control valve regulates the amount of gas delivered to a diaphragm, preferably an inflatable balloon diaphragm, in the exhalation valve by selectively venting gas from the exhalation control system. As the pressure on the diaphragm increases relative to the pressure in the patient circuit, the resistance of the exhalation valve to the flow of gases from the patient circuit increases, thereby increasing the amount of effort required by the patient to exhale and thereby retaining an appropriate pressure in the patient's airway to resist collapse of the lungs and to promote breathing at the beginning of inhalation. Excess gas from the diaphragm is exhausted through the PEEP control valve to the atmosphere. Exhalation is accomplished by the passage of the exhaled breath through an exhaust opening through exhalation valve, which is located in the patient's circuit. Preferably, the patient's circuit is connected to the exhalation control system by a signal conduit between the PEEP valve and the exhalation control valve, an airway conduit delivering breathable gas to the exhalation control valve, and a conduit leading to a pressure sensor.

As a result, the movement of the piston directly corresponds to the inhalation and exhalation of the patient pneumatically connected to the ventilator, with the desired amount of oxygen enrichment provided to aid the patient's respiration. The enrichment is provided notwithstanding the sinusoidal flow of breathable gas into the piston ventilator because the amount of oxygen added to the cylinder is constantly monitored and controlled in a closed loop system and compared to a target value for total oxygen. The exhalation system also permits pneumatic, rather than mechanical, control of the exhalation valve and permits continuous automatic adjustment according to the positive end expiratory pressure sensed in the patient circuit. These and other advantages will be readily apparent to those skilled in the art with reference to the drawings, and description set forth below.

BRIEF DESCRIPTION OF THE DRAWINGS

FIG. 1 is a schematic diagram of a piston ventilator system including a PEEP control exhalation system, with pneumatic connections shown in solid lines and electric connections shown in dashed lines;

FIG. 2 is a simplified diagram of the PEEP control exhalation system showing the exhalation valve and the inflatable diaphragm therein;

FIG. 3 is a block diagram of various components of the controller shown in FIG. 1 in operative relationship to controlled components of the PEEP control exhalation system; and FIG. 4 is a block diagram of various components of the controller shown in FIG. 1 in operative relationship to controlled components of the oxygen blending and piston-driven pressurization system.

DESCRIPTION OF THE PREFERRED EMBODIMENT

Referring now to the drawing, a ventilator system 10 particularly useful for assisting respiration in medical patients is shown schematically in FIG. 1 and broadly includes an oxygen blending module 12, a primary piston-driven pressurization system 14, a secondary make-up gas module 16, a controller 18, a patient circuit 20 and an exhalation control system 21 having a positive end expiratory pressure (PEEP) control valve 22. The patient circuit is detachably mounted to the exhalation control system 10 and thus is located outside an enclosure and in immediate proximity to the patient 26. The patient circuit 20 includes an exhalation control valve 24. The ventilator system 10 is particularly useful in delivering air with enhanced oxygen content in a patient-assist mode to a medical patient 26 with incomplete respiratory capabilities, but it may be appreciated that the ventilator system 10 may employ other breathable gases, for instance helium or nitrogen which may be blended with oxygen, as circumstances dictate.

The oxygen blending module 12 is connected to a source of pressurized oxygen 28 such as bottled oxygen or a connection to a central oxygen source by a fitting 30. The oxygen received from the source 28 passes through a check valve 32 and a filter 34, e.g. 40 micron mesh filter, and is divided into first and second paths 36 and 38. The first path 36 leads to the primary pressurization system 14, while the second path 38 leads to the exhalation control system 21.

The oxygen provided by the first path 36 passes from a pressure regulator 40 for providing the supplied oxygen at a substantially constant desired pressure, and then to primary oxygen control valve 42. Preferably, the regulator 40 limits pressure of the oxygen downstream from the regulator to 55 psi to maximize output, although lower settings are permissible. Advantageously, the primary oxygen control valve 42 is a station, illustrated schematically in FIG. 1 as a single valve, and is provided as two parallel current-controlled voltage sensitive orifice (VSO) valves. Current rather than voltage is used to control the VSO valves because it is less subject to variations due to temperature. The primary oxygen control valve station 42 is electrically coupled to controller 18 for receiving control signals and transmitting valve position information. A gas flow sensor 44 is provided downstream from primary oxygen control valve 42 to monitor the flow of oxygen therepast. The gas flow sensor 44 is preferably provided as a low flow gas sensor in parallel with a flow inducing restrictor to provide a larger full scale flow capacity than the low flow gas sensor alone. The gas flow sensor 44 is electrically connected to the controller 18 for providing a signal thereto.

The primary piston-driven ventilation system 14 includes a cylinder 46 and a reciprocating piston 48 presenting a chamber 50 between the piston 48 and the cylinder 46. The piston 48 is coupled to an arm 52 which functions as a cam to move the piston 48 vertically within the cylinder 46 at the greatest rate at the middle of the stroke and at the smallest rate at the beginning and end of the stroke. The speed of the piston 48 during retraction is thus sinusoidal corresponding to the cosine of the angle between the arm and the horizontal as illustrated in FIG. 1. The arm 52 is coupled to a gear box 54 driven by a bidirectional motor 56. That is to say, the motor is capable of both clockwise and counterclockwise movement, whereby the arm 52 does fully rotate but rather reverses direction during transition between the protracting and retracting stroke and vice versa. An end of travel sensor 58 is adjustably mounted for operative engagement with the piston 48 at the bottom of the retracting stroke and electrically coupled to the controller 18 to signal the controller 18 to initialize the position of the motor 56 and thus the piston 48 at start up and as a safety device during continued operation. By initializing the position of the motor 56, the controller 18 controls the operation of the motor 56 to change its direction of rotation and thus the length of the stroke of the piston 48 within the cylinder 46 at the appropriate position based on the motor position and a preselected total volume setting provided by the operator to the controller 18. The adjustment feature permits the amount of enriched oxygenated air or other gas supplied to the patient 26 to be varied based on the patient's lung capacity. The motor 56 is preferably a brushless direct current motor which is electrically coupled to the controller 18 to provide a continuous signal corresponding to the number of revolutions and position of the motor drive and thus the arm 52. Air or other breathable gas is supplied to the primary piston-driven ventilation system 14 from the ambient air inlet 59 which passes through a filter 60, e.g. a 0.3 micron filter, and through a check valve 62. The air is mixed with the oxygen supplied from the oxygen blending module 12 in the chamber 50, and then discharged through check valve 64 before passing through another filter 66, such as a 50 by 250 mesh filter leading to the exhalation control system 21.

The secondary make-up gas module 16 primarily includes a low-pressure/low-volume blower 68 delivering air through a check valve 70 into the patient circuit 20 downstream from filter 66 and is prevented from flowing back into the chamber 50 by check valve 71. The blower 68 typically operates constantly to supply a flow of breathable gas such as air obtained from the ambient air and at higher speeds may generate as much as 20 cm $H_2O$ peak pressure to make-up air lost through leakage of up to 10 liters per minute of air in the patient circuit, e.g., around a tracheal tube or the like. The operating speed of the blower 68 is controlled by the controller 18 in response to a signal corresponding to the pressure in the patient circuit 20 provided to the controller as sensed by a pressure sensor 98. The blower 68 thus not only compensates for leaks in the system but also maintains PEEP levels and provides a flow, when a patient initiates a breath, for which to trigger a breath.

The controller 18 includes a microprocessor 72 which is programmed with operating instructions. As shown in FIG. 4, the controller 18 also includes a flow sensor signal conditioner 74 which receives input from the flow sensor 44, with the signal being delivered to the microprocessor 72 via an analog to digital converter 76. Similarly, the microprocessor 72 provides a signal to a blender valve drive 78 which provides sufficient current to operate the VSO valves of the primary oxygen control valve station 42 through a digital to analog converter 80. Also as shown in FIG. 4, the microprocessor 72 receives a signal from a motor position monitor 82 operatively connected to motor 56 which in turn senses the number of revolutions and position of the motor 56 and thus the arm 52 and piston 48 and in turn signals the motor 56 to protract or retract the piston 48. As shown in FIG. 3, the controller 18 includes other components to perform functions relating to sensing the PEEP and operating the PEEP valve 22 in response thereto. The controller also includes a pressure sensor signal conditioner 112 which receives input from the first pressure sensor 98, with the signal being delivered to the microprocessor 72 via an analog to digital converter 114. Similarly, the microprocessor 72 provides a signal to a PEEP valve controller 116 mounted on PEEP valve 22 through a digital to analog converter 118. The PEEP valve 22 is then in turn connected to the exhalation valve 24 by a signal conduit 91 as shown in FIG. 1 to provide resistance based on PEEP by providing a pneumatic signal and thereby controls the PEEP at the end of the exhalation of the patient's breath.

The exhalation control system 21 receives blended air from filter 66 and make up air from blower 68 through check valve 70. Excess pressure may be relieved by actuating manual pressure relief valve 84. The second path 38 is provided as a conduit which advantageously may be connected to regulator 40 to obtain oxygen at 55 psi instead of directly from the supply 28 which typically is at 80 psi, although such direct routing is possible. The routing of the second path 38 from regulator 40 permits the use of a pressure regulator 86 which steps down the pressure from 55 psi to about 15 psi. Oxygen provided through second path 38 and through pressure regulator 86 is then directed through make-up oxygen control valve 88 for delivery through a flow restrictor 128 to the exhalation control system 21 for delivery to the patient circuit 20. Make-up oxygen control valve 88 may be provided as either a circuit-controlled voltage sensitive orifice valve, or alternatively a digital valve which is electrically connected to controller 18 as is blower 68. The amount the make-up oxygen control valve 88 is permitted to open to admit oxygen from second path 38 is proportional to the flow of air or other breathable gas delivered by the blower 68 as controlled by the controller 18 based on the desired total amount of oxygen to be delivered to the patient. It is intended that the pressure of the oxygen supplied through regulator 86 will exceed the pressure generated by the blower 68 to ensure a constant positive flow of oxygen enriched air through the patient circuit 20.

The exhalation control system 21 includes the PEEP control valve 22, signal conduit 91, a flow restrictor 94, a flow sensor 96, a first pressure sensor 98, a second pressure sensor 102, and a filter 104. The PEEP control valve 22 serves to vent excess air to the atmosphere through vent 90 to regulate the pressure on the diaphragm side of the exhalation control valve 24, which in turn regulates in the patient circuit 20 to the PEEP setting entered by the operator. The PEEP valve 22 is electrically coupled to the controller 18 to regulate the amount of air permitted to be vented through vent 90. When the PEEP valve is at full bypass or open, an inflatable diaphragm 110 in the exhalation control valve 24 of the patient circuit will be fully deflated giving nearly a 0 cm $H_2O$ PEEP. When the PEEP valve 22 is fully closed, the exhalation valve 24 is closed to prevent gas from passing through the exhalation valve 24 to exhaust 92 and thus gas cannot escape during inhalation. Under these conditions, pressure in the patient circuit 20 and the exhalation control system 21 can be arbitrarily large depending on the amount of gas contained in the available volume until pressure relief valve 84 is activated. Similarly, the PEEP control valve 22 is pneumatically coupled to exhalation control valve 24 to decrease the pressure in the patient circuit 20 when the PEEP pressure rises above the predetermined valve. On the other hand, when the PEEP pressure falls below the predetermined valve, the controller 18 signals the blower 68 to increase its speed and thereby increase the pressure in the patient circuit. As a safety measure the PEEP valve 22 is normally open to deflate the inflatable diaphragm 110 and allow the patient to breathe in the event of a failure. The PEEP control valve 22 is pneumatically connected to the exhalation control valve 24 by a signal conduit 91. As shown in FIG. 2, the PEEP control valve 22 is pneumatically connected to the exhalation control valve 24 includes a body 106 defining therein a enclosure 108 and the inflatable diaphragm 110 within the enclosure 108 which regulates the restriction through which the patient 26 must exhale air delivered to exhaust 92 to the atmosphere. One exhaust valve 24 which has been found to be acceptable for use is commercially available as part no. 6350 which is a component of patient circuit Model No. 6262 available from Nellcor Puritan Bennett of Pleasonton, Calif.

Oxygen enriched air is delivered to PEEP valve 22 through a flow restrictor 94, with the main flow of air delivered by the primary piston-driven ventilation system through a flow sensor 96 which monitors the delivery of air to the patient. The size of the opening of the PEEP valve 22 and the pressure in the patient circuit 20 as determined by first pressure sensor 98 determine the rate of flow of gases out of the PEEP valve 22. Because the PEEP valve 22 and the restrictor 94 are in series, the flow of gas out of the PEEP valve 22 is also the flow through the restrictor 94, plus or minus any minimal flow of gas to or from the diaphragm 110 through the signal conduit. The rate of flow of the gases through the restrictor 94 induces a pressure drop across the length of the restrictor 94. This pressure on the backside or signal conduit side of the diaphragm 110 to be less than the pressure at the patient side (i.e the front side) of the diaphragm 110. This pressure difference reduces the resistance of the exhalation valve 24, allows gases in the patient circuit 22 escape out of the exhalation valve 24, and ultimately decreases the pressure in the patient circuit 20. By controlling the rate of flow of gases through the restrictor 94, the pressure in the patient circuit 20 and PEEP may also be controlled.

During exhalation, the piston 48 is retracted and thus air or other breathable gas is supplied to both PEEP valve 22 and exhalation control valve 24 by a combination of make-up air from blower 68 and oxygen supplied through patient circuit oxygen control valve 88, and from the exhalation of the patient 26. A first pressure sensor 98 is in immediate proximity to the patient 26 in the conduit delivering oxygen-enriched air to the patient 26, and is electrically connected to the controller 18 to signal the PEEP valve 22 how much air is to be exhausted to the atmosphere through exhaust 92, and therefore how much of the make-up air and breath exhaled by the patient is delivered to the exhalation control valve inflatable diaphragm 110. The first pressure sensor 98 is electrically connected to the controller 18 and thus provides the controller 18 with a signal corresponding to the pressure of the gas being provided to the patient 26 during inhalation, and PEEP at the end of exhalation. A second pressure sensor 102 is electrically connected to the controller 18 and provides a backup and validation of the first pressure sensor 98 by monitoring the pressure in the exhalation control system 21 and providing a second pressure signal to the controller.

The PEEP valve 22 is normally open and indirectly controls the resistance of the exhalation valve 24 to the flow of gas from the breathing circuit to the atmosphere. By increasing or decreasing this resistance, the exhalation valve 24 can decrease or maintain the amount of gas in the patient circuit and thereby decrease or maintain the pressure in the patient circuit 20. The PEEP valve 22 regulates the pressure applied to the exhalation valve 24 by controlling the amount of air delivered from the patient circuit 20 to the exhaust 92. The more gas delivered by the PEEP valve 22 to the vent 90, the lower the pressure on the diaphragm on the exhalation valve 24 that covers the exhalation opening 100 of the exhalation control valve 24. The greater the restriction in the PEEP valve 22 and thus the less gas delivered to the vent 90, the greater the pressure on the diaphragm 110 of the exhalation control valve 24 and thus the greater the expansion of the diaphragm 110 within the enclosure 108 thereby reducing the size of the restriction to increase the resistance provided during exhalation by the patient 26. The amount of resistance to exhalation is proportional to the pressure of the gas supplied to the diaphragm 110 and thus proportional to the amount the PEEP valve 22 is open. The signal supplied to open or close the PEEP valve 22 by the controller 18 is determined by the first pressure sensor 98.

The primary flow sensor 98 provides a signal corresponding to the volume ($V_T$) of the mixed gas leak in the patient circuit 20. The volume of oxygen ($O_2$) introduced is known by introducing $O_2$ gas of known pressure upstream of a known orifice size for a specific period of time. Alternatively, a VSO may be used in place of the fixed orifice and a digital valve. The $O_2$ concentration of make-up gas is then known via:

$$V_T = V_{AIR} + V_{O2}$$

$$O_2\% = 79(V_{O2} \div V_T) + 21$$

The controller in turn sends operating signals to blower 68 and patient circuit oxygen control valve 88. A filter 104, such as a 40 mesh filter, provides final filtration of the air with enriched oxygen prior to deliver to the patient.

The patient circuit 20 is connected to the exhalation control system 21 by flexible conduits 120, 122 and 124 which lead to hose connectors 126 which are respectively operatively connected to the first pressure sensor 98, the filter 104 delivering breathable gas to be inhaled by the patient, and the signal conduit 91 leading to PEEP valve 22.

In use, the ventilator system 10 hereof provides respiratory assistance to patient 26 so that the respiration rate of patent 26 directly corresponds to the rate of reciprocation of the piston 48 within the chamber 50. Thus, with each protracting movement of the piston 48 within the cylinder 46, patient inhales, and with each retracting stroke of the piston 48 within the cylinder 46, the patient exhales. Prior to operation of the ventilator system, the operator selects and sets the controller 18 at a desired level of oxygen enrichment, for example within a range of 21% to 100% total oxygen received by the patient and additionally selects a target pressure level for PEEP within a typical range of 0 cm $H_2O$ to 20 cm $H_2O$.

During each retracting stroke of the piston 48, the motor position monitor 82 signals the position of the piston 48 within the cylinder 46 and permits the controller 18 to calculate the volume of the chamber 50. For any desired amount of oxygen enrichment, this produced a corresponding calculation of the amount of added oxygen which should be present in the chamber. The calculation of volume and thus the amount of added oxygen present in the chamber 50 is continuously updated during the retracting stroke of the piston 48. Because the speed of retraction of the piston 48 is not linear but rather sinusoidal, the volume in the chamber 50 changes sinusoidally.

Flow sensor 44 thus determines the flow rate of oxygen delivered to chamber 50 on a continuous basis. Its signal is received by the controller 18 and the flow rates are integrated to yield the amount of oxygen actually delivered to the chamber 50. If the controller 18 determines that the accumulated oxygen delivered to the chamber is insufficient, it signals the primary oxygen control valve station 42 to open and permit additional oxygen to flow past flow sensor 44. If this produces oxygen in the chamber 50 in excess of the target amount prior to the end of the retracting stroke as determined by the integrated value, calculated by the controller from the flow rates determined by flow sensor 44, the controller signals the primary oxygen control valve station 42 to close and thereby reduce the flow of oxygen past flow sensor 44 and delivered to chamber 50.

During the retraction stroke of the piston 48, the patient exhales. Exhalation by the patient is primarily delivered through exhalation control valve 24 to exhaust 92. The inflation of the diaphragm within the exhalation control valve 24 causes the flow of exhaled air through the exhalation opening 100 to be restricted, and the patient must exert some effort to overcome the restriction depending on the pressure of the gas supplied to the inflatable diaphragm. The amount of the restriction may be controlled by the signal supplied by the controller 18 to the PEEP valve 22 to determine the amount of air permitting to vent therefrom. Because of leakage around tracheal tubes in tracheostomies or through conduit connections, the majority of the air supplied to the exhalation control valve 24 is delivered by blower 68. Because a portion of the air remaining in the inhalation control system 21 will be inhaled when the piston 48 protracts, it is desirable to ensure that the air inhaled by the patient 26 is properly oxygenated. To that end, supplemental oxygen is delivered to the patient circuit 20 through make-up oxygen control valve 88 and its opening and closing as well as the speed of and thus the flow of gas delivered by the blower are determined by the controller 18 based on the signal provided by the first pressure sensor 98. If a PEEP setting of zero is provided to the controller 18, the blower 68 will shut off and the make-up oxygen control valve 88 will be closed.

In the event of a leak (up to 10 liters per minute), and in the presence of PEEP (up to 20 cm $H_2O$), the blower 68 is energized by the control logic to provide the make-up air to fulfill the requirements of the leak. While doing this, PEEP pressure is maintained. The air provided by the blower 68 is not enriched by additional oxygen, but supplemental oxygen may be supplied through the make-up oxygen control valve 88 as described above.

Once the piston 48 reaches the end of its retracting stroke as sensed by the motor position monitor and determined by the controller 18 based on motor position and speed and the preset overall volume desired for delivery to the patient 26, the controller 18 signals the motor 56 to reverse its direction and begin protraction of the piston 48 within the cylinder 46. As the piston protracts, oxygen-enriched air is expelled from the chamber 50 through the check valve 64 for delivery to the patient circuit 20 and ultimately inhalation by patient 26 after passage through filter 104. Thus, protraction of the piston 48 corresponds to inhalation 26 by the patient due to the delivery of pressurized air to inflate the patient's lungs.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby states their intent to rely on the Doctrine of Equivalents to determine and assess the reasonably fair scope of their invention as pertains to any apparatus not materially departing from but outside the literal scope of the invention as set out in the following claims.

We claim:

1. A patient ventilator comprising:
   a piston and cylinder assembly;
   a patient circuit for delivering gas from said piston and cylinder assembly
      to a patient during patient inhalation, said patient circuit including:
      an exhalation valve including a valve element responsive to a pneumatic signal for shifting between an open position, a closed position, and a range of intermediate positions in corresponding relationship to said pneumatic signal;

a signal conduit in fluidic communication with said exhalation valve for delivering gas to said valve element as said pneumatic signal;

a PEEP valve coupled with said signal conduit for selectively venting gas received by the patient circuit for selectively altering said pneumatic signal;

a pressure sensor coupled with said patient circuit for sensing the pressure therein as the PEEP pressure and for producing a PEEP pressure signal representative thereof;

means positioned upstream of said PEEP valve for creating a pressure differential between the gas pressure in the signal conduit and the gas pressure at the pressure sensor; and a controller coupled with said pressure sensor for receiving said PEEP pressure signal and comparing said PEEP pressure to a target pressure, and responsive thereto for operating said PEEP valve during patient exhalation in order to vent gas selectively from said signal conduit for altering said pneumatic signal and thereby the position of said exhalation valve and for altering said PEEP pressure to achieve said target pressure.

2. A patient ventilator as set forth in claim 1, wherein said valve element comprises a diaphragm in operative communication with said signal conduit.

3. A patient ventilator as set forth in claim 2, wherein said diaphragm is an inflatable diaphragm and said pneumatic signal comprises pressurized air received into said diaphragm.

4. A patient ventilator as set forth in claim 1, including a secondary pressure source of gas in addition to said piston and cylinder assembly for providing positive pressure gas to said patient circuit.

5. A patient ventilator as set forth in claim 4, wherein said secondary pressure source comprises a blower.

6. A patient ventilator as set forth in claim 5, wherein said blower is operatively coupled to said controller for regulating the delivery of positive pressure gas to said patient circuit.

7. A patient ventilator as set forth in claim 4, wherein said secondary pressure source includes a supplemental source of oxygen and a source of positive pressure ambient air for mixing with oxygen provided by said supplemental source.

8. A patient ventilator as set forth in claim 7, including a supplemental oxygen valve operatively coupled to said controller for controlling the amount of supplemental oxygen delivered to said patient circuit.

9. A patient ventilator as set forth in claim 1, said pressure differential creating means including a flow restrictor located upstream from said valve for selectively venting gas for providing a pressure drop across the length of said flow restrictor.

10. A patient ventilator as set forth in claim 1, including an oxygen source upstream from said piston and cylinder assembly for delivering oxygen thereto.

11. A patient ventilator as set forth in claim 10, including an oxygen flow sensor located intermediate said oxygen source and said piston and cylinder assembly and in communication with said controller for providing an oxygen flow signal thereto, and an oxygen control valve located intermediate said oxygen source and said oxygen flow sensor and in communication from said controller for controlling the amount of oxygen delivered from said oxygen source to said piston and cylinder assembly responsive to the oxygen flow signal and the operative position of a piston within a cylinder of said piston and cylinder assembly.

12. In a ventilator for providing gas under pressure to a user for breathing, the ventilator including a primary piston-driven pressurization system and a patient circuit, the improvement comprising:

a secondary make-up air pressurization system for supplying pressurized air to said patient circuit; and an exhalation control system operatively coupled to said secondary make-up air pressurization system, said exhalation control system including a first sensor for sensing a PEEP pressure value in said patient circuit, a gas-venting valve, a exhalation valve including a diaphragm for providing exhalation resistance, and a conduit for conveying a signal to said diaphragm of said exhalation valve, said conduit operatively connecting said secondary pressurization system to said diaphragm, wherein said first sensor is in operative communication with said gas-venting valve for actuating said gas-venting valve through a range between an open and a closed position in response to said sensed value and thereby control the signal conveyed to said diaphragm through said conduit.

13. A ventilator as set forth in claim 12, wherein said diaphragm is an inflatable balloon diaphragm.

14. A ventilator as set forth in claim 12, wherein said signal conveyed by said conduit is a pneumatic signal.

15. A ventilator as set forth in claim 12, including a controller for calculating the PEEP pressure in response to said sensed value, receiving a preselected target PEEP value, comparing the sensed value to the target value, and controlling said gas-venting valve in response to said comparison.

16. A method of providing breathable gas to a patient comprising the steps of:

providing a piston ventilator including a patient circuit, a piston and cylinder assembly for providing a primary source of pressurized gas to said patient circuit, a secondary source of pressurized gas in communication with said patient circuit, a pressure sensor in said patient circuit in proximity to said patient, a gas vent valve, a controller, and an exhalation valve having a valve element shiftable between an open position, a closed position and a plurality of intermediate positions;

providing a pneumatic signal from said patient circuit to said element of said exhalation valve to control the resistance of the exhalation valve during the exhale portion of the patient's breath;

sensing the PEEP in the patient circuit by said pressure sensor;

providing a signal from said pressure sensor to said controller corresponding to the sensed PEEP;

comparing said sensed PEEP to a preselected target PEEP in said controller;

providing a signal from said controller to said gas vent valve to adjust the venting characteristics of said gas vent valve and thereby alter said pneumatic signal;

delivering said altered pneumatic signal to said element of said exhalation valve to change the resistance of the exhalation valve to patient exhalation.

* * * * *